United States Patent [19]

Nakata et al.

[11] Patent Number: 5,232,832
[45] Date of Patent: Aug. 3, 1993

[54] ANTIBODY REACTIVE TO HAMSTER IMMUNOGLOBULINS AND ASSAY USING SAME

[75] Inventors: Motomi Nakata, Osaka; Hiroshi Eto, Bunkyo; Yukihito Hasunuma, Bunkyo; Hideo Yagita, Bunkyo; Ko Okumura, Bunkyo, all of Japan

[73] Assignee: Sumitomo Electric Industries, Ltd., Osaka, Japan

[21] Appl. No.: 797,957

[22] Filed: Nov. 26, 1991

[30] Foreign Application Priority Data

Nov. 30, 1990 [JP] Japan .................................. 2-337575

[51] Int. Cl.⁵ .......................................... G01N 33/535
[52] U.S. Cl. ...................................... 435/7.5; 435/7.9;
435/172.2; 436/513; 436/536; 436/543; 436/548
[58] Field of Search ...................... 435/172.2, 7.9, 7.5; 436/513, 536, 543, 548

[56] References Cited

PUBLICATIONS

Leptin et al–Chem. Abst. vol. 101 (1984) p. 88588K.
Bird et al–Chem. Abst. vol. 101 (1984) p. 22827m.
S. Bright et al, "Generation and Characterization of Hamster–Mouse Hybridomas Secreting Monoclonal Antibodies With Specificity for Lipopolysaccharide Receptor", The Journal of Immunology, vol. 145, No. 1, Jul. 1, 1990, Baltimore, pp. 1–7.
G. Kohler et al, "Continuous Cultures of Fused Cells Secreting Antibody of Predefined Specificity", Nature, vol. 256, Aug. 7, 1975, London, pp. 495–497.
T. Kayano et al, "Growth of Rat–Mouse Hybridoma Cells in Immunosuppressed Hamsters, An Easy and Effective Method to Prepare Monoclonal Antibodies from heterohybridoma Cell Lines", Journal of Immunological Methods, vol. 130, No. 1, 1990, Amsterdam, The Netherlands, pp. 25–31.
T. Springer et al, "Monoclonal Antibodies Specific for Rat IgG1, IgG2a, and IgG2b Subclases, and Kappa Chain Monotypic and Allotypic Determinants: Reagents for Use With Rat Monoclonal Antibodies", Hybridoma, vol. 1, No. 3, 1982, New York, pp. 257–273.

*Primary Examiner*—Sam Rosen
*Attorney, Agent, or Firm*—Cushman, Darby & Cushman

[57] ABSTRACT

A monoclonal antibody specifically reactive to hamster immunoglobulins, a hybridoma producing said monoclonal antibody, and an immunoassay utilizing said monoclonal antibody are provided. The monoclonal antibody is useful in an immunoassay as a secondary antibody to a hamster-derived primary antibody or antiserum raised against various antigens.

6 Claims, 2 Drawing Sheets

ANTIBODY REACTIVE TO HAMSTER IMMUNOGLOBULINS AND ASSAY USING SAME

FIELD OF THE INVENTION

The present invention relates to a novel monoclonal antibody specifically reactive to hamster immunoglobulins, a hybridoma producing said monoclonal antibody, and an immunoassay using said monoclonal antibody.

PRIOR ART

The studies on immune system and mechanism of development of immunology-associated diseases have been conducted mainly using mouse immunocytes and utilizing antibodies against various surface antigens on the cells. Immunocytes have various antigens on their surfaces, and these surface antigens vary according to the kinds, functions, and degrees of differentiation of immunocytes. Accordingly, by detecting the presence of particular surface antigens on the cells using monoclonal antibodies raised against each of those surface antigens, typing of immunocytes has become easier. This has contributed much to the basic studies of immunology.

Previously, most of the antibodies against surface antigens of mouse immunocytes have been obtained by immunizing a rat with mouse immunocytes as an antigen. Recently, a new method where a hamster is used to be immunized has been investigated for developing antibodies against surface antigens of mouse immunocytes.

For studying surface antigens of mouse immunocytes using the antibodies therefor, an immunoassay has previously been conducted, in which the antibodies are labelled with any of a fluorochrome such as FITC (fluorescein isothiocyanate) and PE (phycoerythrin), an enzyme such as HRPO (horseradish peroxidase) and AP (alkaline phosphatase), or a radioisotope such as $^{125}$I, $^{14}$C and $^3$H, and the antibodies reacted with the surface antigens are detected by suitably labelling the antibodies ("Men-ekigaku Jikken Nyuumon", VIII, Labelled Antibody; Gakkai Shuppan Center, 1981).

An immunoassay which utilizes a primary antibody raised against an antigen and a second antibody, i.e., anti-Ig antibody, prepared using the primary antibody as an antigen is also conventionally conducted in the art.

As described above, most of the previous antibodies raised against surface antigens of mouse immunocytes have been derived from a rat. However, there exists a problem resulting from the fact that a rat and mouse are a closely related species each other. Thus, a certain antigen of mouse immunocytes has a significantly high homology to a corresponding antigen of rat immunocytes, and therefore, immunization of a rat with such antigen of mouse immunocytes may fail to give any antibody. For this reason, a hamster which is a species less related to mouse has recently been employed for preparation of an antibody against a mouse antigen. However, when the hamster antibody is used as a primary antibody, there exists no appropriate second antibody so far. Thus, when the hamster antibody was used instead of a rat antibody, no anti-hamster immunogloblin monoclonal antibody which is reactive to all of hamster immunogloblins was available, and only an antiserum (polyclonal antibody) obtained by immunizing a rabbit or goat with a hamster immunogloblin was available. The antiserum has a cross reactivity not only with hamster immunogloblins, but also with rat and mouse immunogloblins and mouse immunocytes. Furthermore, there exists a problem of not being able to efficiently produce a hamster immunogloblin for detection of a surface antigen of mouse immunocytes. Accordingly, it is very significant to obtain a monoclonal antibody reactive to every hamster immunogloblin, and to develop a method to produce said monoclonal antibody industrially, but such monoclonal antibody has not been succesfully obtained so far.

BRIEF DESCRIPTION OF THE INVENTION

Thus, the present invention is to provide a monoclonal antibody raised against hamster immunogloblins as mentioned above. Moreover, it is an important object of the invention to provide a method of producing said monoclonal antibody industrially, and to provide an immunoassay utilizing said monoclonal antibody.

DETAILED DESCRIPTION OF THE INVENTION

Figure 1:
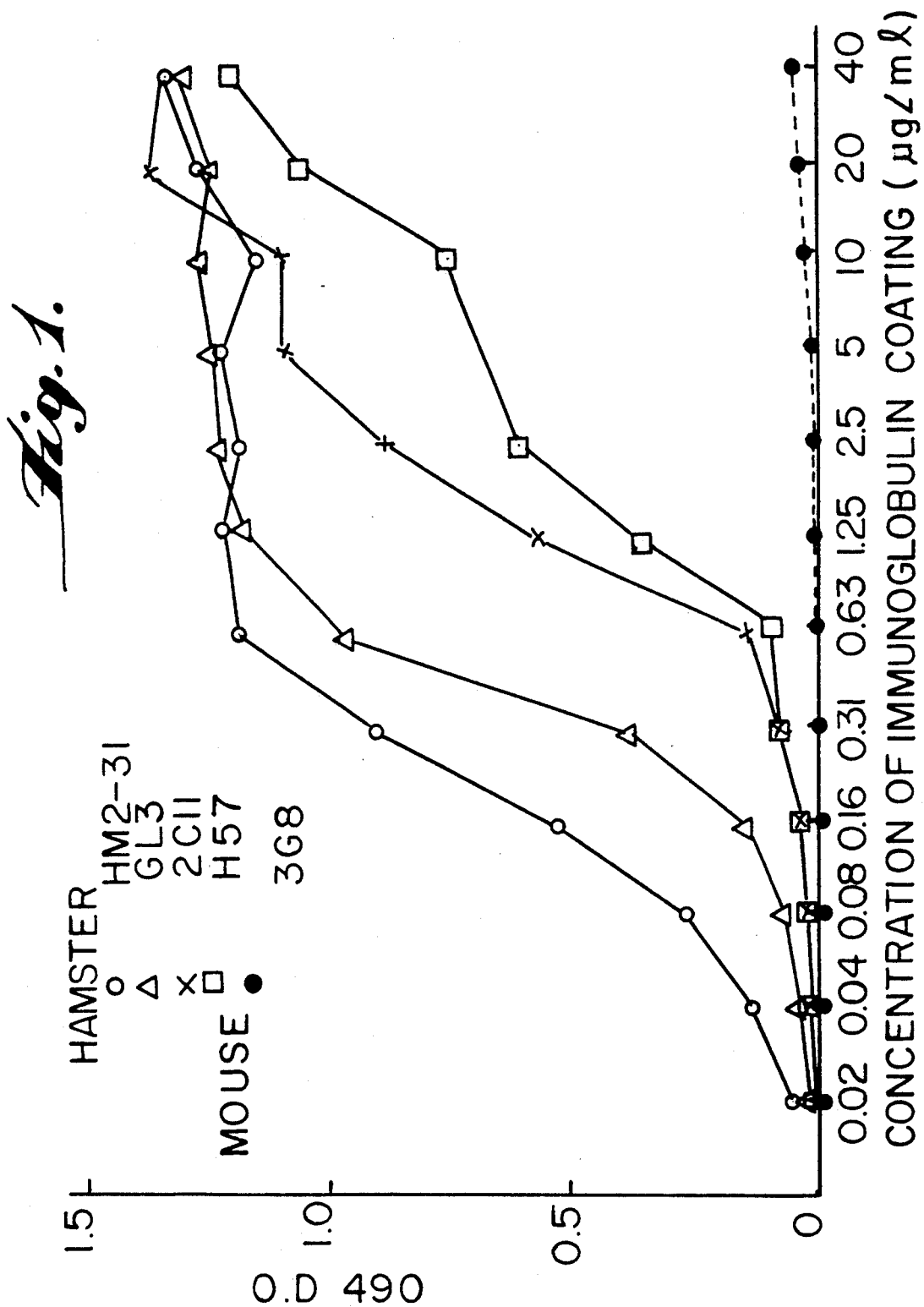
FIG. 1 shows the reactivity of the present monoclonal antibody to the hamster immunogloblins and to the mouse immunogloblin. The reactivity was examined by ELISA.

The present inventors have made an intensive investigation to obtain a monoclonal antibody against hamster immunogloblins having the characteristics as described above, and found that it is advantageous to utilize a hybridoma, that is, fused cells of antibody-producing cells of a rodent animal immunized with a hamster antibody and myeloma cells of a rodent animal. The present invention has been accomplished based on the above findings.

The monoclonal antibody and the hybridoma producing said monoclonal antibody according to the present invention can be produced as follows:

a) immunizing a rodent animal with a hamster immunogloblin as an antigen;

b) fusing antibody-producing cells from said immunized rodent animal with myeloma cells of a rodent animal;

c) selecting a hybridoma producing a monoclonal antibody reactive to all of the hamster immunogloblin used in step a) and other hamster immunogloblins; and d) cultivating the hybridoma selected in step c) under a suitable condition, and recovering said monoclonal antibody.

The immunization of a rodent animal of the step a) can be conducted by administering as an antigen a hamster immunogloblin such as a monoclonal antibody against mouse CD2 molecule, mouse CD3 molecule, mouse TCRαβ molecule or mouse TCRYγδ molecule to the animal, and further treating the animal with the same antigen at an appropriate intervals. A preferred hamster immunogloblin is a hamster monoclonal antibody reactive to mouse CD2 molecule. The rodent animal to be immunized includes mouse, rat, guinea pig, etc. Preferably, rat, especially F344 rat (Nihon Charles River) is used. Typically, the antigen is mixed with complete Freund's adjuvant and injected to the animal.

The cell fusion of the step b) can be carried out by a conventional method using antibody-producing cells of the rodent animal immunized in the step a) and myeloma cells of the rodent animal. The antibody-producing cells include spleen cells, lymph node cells, and peripheral lymphocytes, and preferably spleen cells or lymph node cells are used. The myeloma cells of the rodent animal include rat Y3, mouse P3-X63-Ag8.653, P3-X63-Ag8-Ul, NS-1, SP2/0-Ag14 and PAl, and preferable myeloma cells are mouse 8-azaguanine resistant cell line P3-X63-Ag8-UI (P3UI).

The cell fusion may be conducted using polyethylene glycol and electroporation procedures.

The selection of the hybridomas in the step c) can be carried out, for example, by enzyme-linked immunosorbent assay (ELISA). Thus, hamster immunogloblins are pipetted into an assay plate and immobilized. Then, the supernatant of the conditioned medium of hybridomas is pipetted into the plate, and allowed to react with the immobilized hamster immunogloblins. Subsequently, an anti-Ig antibody (labelled with biotin) produced against the immunogloblin from the animal used in the immunization of the step a) is added to allow to bind. Then, a peroxidase enzyme is added to allow to bind, and o-phenylenediamine and hydroxy peroxide are added. One can determine by the colouring reaction whether the antibody produced by a particular hybridoma will react with the hamster immunogloblins.

In this manner, one can determine the reactivity of the produced monoclonal antibody to the various hamster immunogloblins, and can select the hybridomas which produce the desired antibody.

The recovery of the monoclonal antibody in the step d) can be carried out by a conventional method, for example, by injecting the hybridomas selected in the step c) into peritoneal cavity of a mouse and then recovering from the ascites fluid of the mouse. Alternatively, the monoclonal antibody may be recovered from a conditioned medium of the hybridoma clones cultivated using a largescale culture apparatus. The antibody recovered may be purified by a conventional purification method, such as ammonium sulfate precipitation, molecular sieve chromatography, ion-exchange chromatography, affinity chromatography, or the like.

Since the monoclohal antibodies of the present invention obtained as described above react specifically with hamster immunogloblins, they can be used in the immunoassay advantageously. Especially, the antibody produced by hybridoma RHIg-87 of the present invention, which is described in more detail in the Example below, can be used advantageously in the immunoassay detecting surface antigens of mouse immunocytes, because said antibody reacts specifically with hamster immunogloblins, and does not cross-react with mouse immunocytes and mouse immunogloblins. In the first assay, the monoclonal antibody of the present invention is labelled with a fluorochrome, enzyme or radioisotope, and used as a second antibody for a primary antibody or an antiserum derived from hamster. In an alternative assay using the monoclonal antibody of the present invention, said monoclonal antibody is bound to biotin and used as a second antibody. To this, a conjugate prepared by binding any of the above labelling substances and avidin or streptoavidin is added and reacted with biotin to allow to easily detect surface antigens of immunocytes. This method is particularly advantageous and convenient because the monoclonal antibody bound to biotin can be applicable to other immunoassay systems by selecting an appropriate conjugate of a labelling substance and avidin or streptoavidin.

The above immunoassay can be conducted according to the known methods in the art. The labelling substances include fluorochromes such as fluorescein isothiocyanate, phycoerythrin or tetrarhodamine isothiocyanate, enzymes such as horseradish peroxidase, alkaline phosphatase, glucose oxidase, $\beta$-D-galactosidase, acetylcholine esterase, lactic dehydrogenase, glucoamylase or telocynase, and radioisotopes such as $^{125}I$, $^{14}C$, $^{3}H$, $^{32}P$, $^{35}S$, $^{45}Ca$, $^{51}Cr$ or $^{131}I$.

As described above, the monoclonal antibody of the present invention makes it possible to avoid labor for binding the labelling substance to various hamster antibodies raised against various surface antigens, and further to realize the more sensitive and stable immunoassays.

The present invention is illustrated by the following Example, but should not be construed to be limited thereto.

EXAMPLE

A. Immunization of Animal

The hamster immunogloblin (100 $\mu$g) purified from the conditioned medium of a hybridoma producing a hamster antibody reactive to mouse CD2 molecule was mixed and emulsified with complete Freund's adjuvant (1:1), and the emulsion was injected into the pad of F344 rats (Nihon Charles River). Six days and nine days after the injection, the animals were boostered by injecting hamster immunogloblin (100 $\mu$g) into the pad of the same rats.

B. Cell Fusion

Three days after the last immunization, one of the above rats was sacrificed and lymph node was removed. The lymph node removed from the inguinae of the both pads was minced, filtered through a mesh, and suspended in RPMI1640 medium to obtain lymph node cells ($1 \times 10^8$ cells) The lymph node cells and mouse 8-azaguanine resistant cell line (hypoxanthine guanine phosphoribosyl transferase defective cell line) P3-X63-Ag8-Ul (P3Ul) [Current Topics in Microbiology and Immunology, 81, 1-7 (1978)] ($2 \times 10^7$ cells) were mixed (approximately 5:1), and centrifuged (1500 rpm, 5 minutes). To the resultant precipitate was added 50% of polyethyleneglycol 4000 (Merk, Co., Ltd.)/ RPMI1640 solution (3 ml), with stirring in a water bath at 37 ° C. over one minute period. To this solution was added RPMI1640 solution (15 ml) with stirring over 6 minutes period to allow to derive cell fusion. After the cell fusion, large quantity of RPMI1640 was added and the supernatant was removed by centrifugation (1500 rpm, 5 minutes). Then, the fused cells were suspended at $1 \times 10^6$ cells/ml in HAT medium [10% FCS (fetal bovine serum)-RPMI1640 medium supplemented with hypoxanthine (100 $\mu$M), aminopterin (0.4 $\mu$M), and thymidine (10 $\mu$M)].

C. Selection of Hybridomas

C-1. Cultivation of Hybridomas

The cell suspension prepared in the above B was plated in 200 $\mu$l aliquots on 5 plates of 96 well microplates and cultivated in a $CO_2$ incubator at 37 ° C. under 5% of $CO_2$ Seven days later, only hybridomas formed colonies and proliferated.

C-2. Detection of Antibodies

After confirming the hybridomas were sufficiently proliferated, the detection of the antibody in the supernatant was carried out by enzyme immunoassay (ELISA) as described below. The hamster anti-mouse CD2 monoclonal antibody which was used in the immunization was diluted into 10 µg/ml with PBS, plated in 50 µl aliquots on an assay plate (Dianatec Immulon 2), and the antigen was immobilized (4° C., over night). Then, the antigen solution was removed, and blocked by adding a blocking solution (Blockace; Dai Nippon Seiyaku Co., Ltd.)(room temperature/ 2 hours). After removing the blocking solution, the supernatant of hybridoma culture (50 µl) was pipetted into the plate and reacted at room temperature for one hour. The plate was washed four times with PBS containing 0.05% Tween 20, and then, to the plate was added 50 µl of the diluted solution (1:100) of anti-rat Ig antibody (Bector Co., Ltd.) labelled with biotin and allowed to bind to the antigen immobilized on the plate (room temperature/ 2 hours). Then, the plate was washed again four times with 0.05% Tween 20-PBS, and an enzyme (peroxidase) was allowed to bind to the plate using Bectastein ABC Kit Elete (Bector Co., Ltd.) (room temperature/ 30 minutes). After the plate was washed again four times with 0.05% Tween 20-PBS, 100 µl of phosphate-citrate buffer solution (pH 5.0) containing 0.4 mg/ml O-phenylenediamine and 0.012% hydrogen peroxide was added onto the plate, and the antibody was detected by coloring reaction. In such a manner; the wells were selected where a hybridoma produces an antibody reactive to hamster antimouse CD2 monoclonal antibody.

C-3. Cloning of Hybridomas

Hybridomas in the wells selected in the above step C-2 were cloned by limiting dilution method. The culture in the wells was diluted so as to obtain 0.5 cell / well with 10% FCS-RPMI1640 medium, and 200 µl aliquotes were pipetted onto 96 well microplate. The cultivation was carried out at 37° C. in the presence of 5% $CO_2$. When the colonies were grown to an appropriate size, the enzyme immunoassay of the step C-2 was repeated to confirm whether the antibody against the above hamster anti-mouse CD2 monoclonal antibody was being produced or not. The hybridoma in the well, which strongly reacted with the hamster-anti mouse CD2 monoclonal antibody, was selected and cloned again by the limiting dilution method.

C-4. Reactivity to various hamster monoclonal antibodies

The reactivities of the antibodies produced by the hybridomas obtained in the above C-3 with various hamster monoclonal antibodies were examined by the enzyme immunoassay of the above C-2. The reactivities of the resulting antibodies with seven hamster monoclonal antibodies, which were monoclonal antibody against mouse CD3 (145-2C11), monoclonal antibody against mouse γδT cell receptor (GL3), monoclonal antibody against mouse αβT cell receptor (H57), and monoclonal antibodies against mouse CD2 molecules (HM2-17, 30, 31, -1-3) were examined. As a result, a hybridoma producing an antibody which was reactive to all of the hamster monoclonal antibodies examined was obtained (FIG. 1). The hybridoma clone was designated as RHIg-87. This clone was deposited to Fermentation Research Institute Agency of Industrial Science and Technology under the accession number of FERM P-11865 (Date of Deposit: Nov. 26, 1990), which has been transferred to a deposit under Budapest Treaty as FERM BP-3649 (Date of Transfer: Nov. 8, 1991).

C-5. Reactivity to mouse immunogloblins

The reactivity of the antibody produced by the hybridoma obtained in the above C-4 with various mouse immunogloblins were examined using the enzyme immunoassay described in the above C-2. The reactivity with three of antibodies which were mouse monoclonal antibody against rat monoclonal antibody (7C4), mouse monoclonal antibody against rat ICAM-1 molecule (IA-29), and immunogloblin in mouse serum was examined (FIG. 1). The results revealed that the antibody obtained in the above C-4 did not react with any of those three antibodies.

C-6. Reactivity to mouse immunocytes

Figure 2:
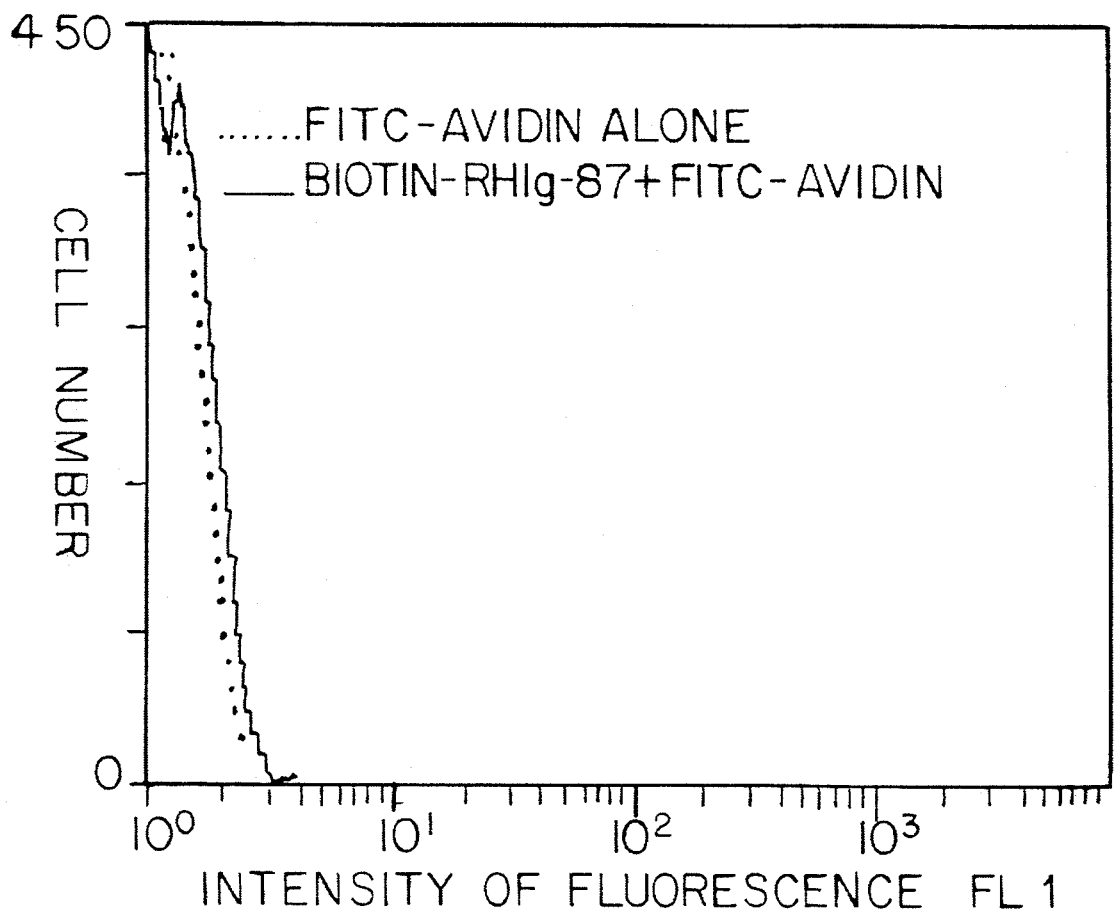
FIG. 2 shows the reactivity of the present monoclonal antibody to Balb/c mouse spleen cells. The reactivity was examined by FACScan using a biotin-labelled monoclonal antibody and FITC avidin.

The reactivity of the antibody produced by the hybridoma obtained in the above C-4 with mouse immunocytes was examined by FACS as described below. Spleen cells were prepared from Balb/c mouse, reacted with the above C-3 antibody labelled with FITC, and fluorescence was determined by FACScan (Becton Dickinson Co., Ltd.). The results showed that the antibody obtained did not react with mouse spleen cells (FIG. 2).

D. Preparation and Purification of Large Amount of Antibody

After being proliferated to a large quantity in 10% FCS-RPMI1640 medium, hybridoma clone RHIg-87 was injected intraperitoneally into a nude mouse ($1 \times 10^7$ cells/mouse). When the cells grew up in the mouse peritoneal cavity and a large quantity of ascites fluid (approximately 10 cc) was produced, the ascites fluid was recovered from the mouse peritoneal cavity to obtain a large amount of the antibody. The antibody was precipitated by adding an equal quantity of saturated ammonium sulfate (100% ammonium sulfate) to the recovered ascites fluid. The resulting precipitate was dissolved in a small amount of PBS (approximately 5 cc), and then purified using Mab trap G TM (Pharmacia Co., Ltd.).

The isotype of the resultant antibody was determined by an enzyme immunoassay where the anti-hamster globlin monoclonal antibody in the supernatant of the hybridoma culture was reacted with anti-rat Ig antibodies (anti-$IgG_1$, $IgG_{2a}$, $IgG_{2b}$, $IgG_{2c}$, IgM) of isotype typing kit (Zimett Co., Ltd.). The results showed that the antibody of the present invention belongs to isotype $IgG_{2b}$

E. SDS-polyacrylamide Gel Electrophoresis of Antibody

Figure 3:
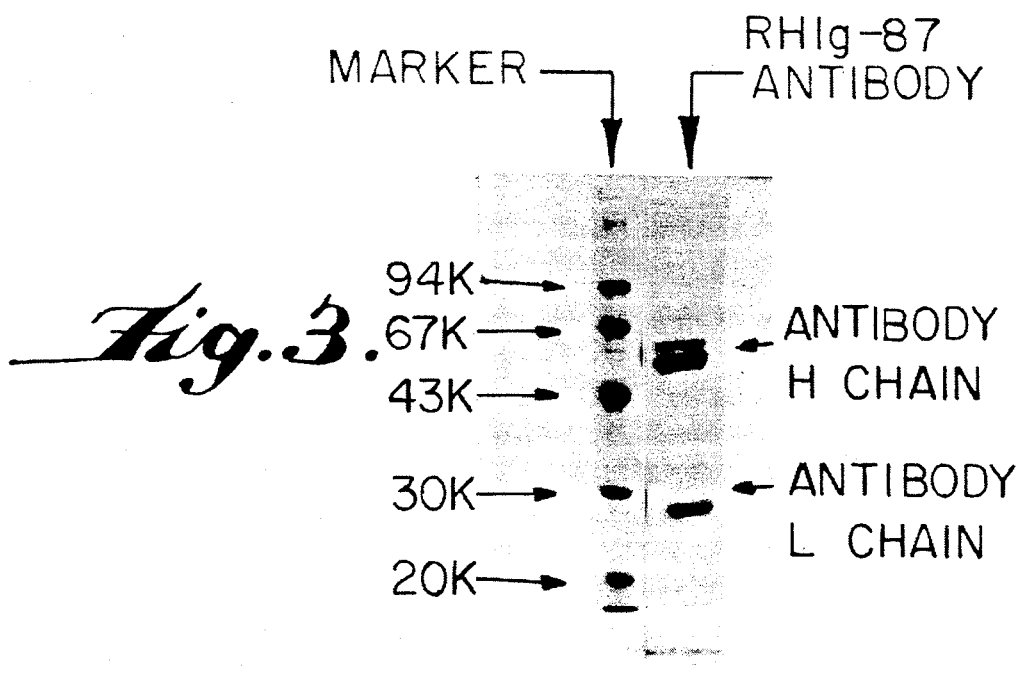
FIG. 3 shows SDS-polyacrylamide gel electrophoresis of the antibody produced by hybridoma RHIg-87.

Ten % SDS-polyacrylamide gel electrophoresis was carried out using the antibody (5 µg) thus obtained. Proteins were stained with Coomassie Brilliant Blue, and the resultant antibody was analyzed. The results showed that RHIg-87 antibody is IgG comprising of H chain of molecular weight of about 50,000 and L chain of molecular weight of about 25,000 (FIG. 3).

As illustrated in the above, the monoclonal antibody of the present invention is useful in an immunoassay since it specifically reacts with hamster immunogloblin. Especially, the antibody produced by hybridoma RHIg-87 of the present invention is useful in detecting surface antigens of mouse immunocytes because it does not cross-react with mouse immunocytes or immunogloblin. Use of such monoclonal antibody as a second antibody provides a convenient immunoassay which does not require binding of a labelling substance to various hamster-derived primary antibodies reactive to surface antigens of mouse immunocytes, and which can stably give a high detection sensitivity. Accordingly, the present invention provides a useful means for numerous experiment systems using mouse.

What is claimed is:

1. A monoclonal antibody produced by hybridoma RHIg-87 (FERM BP-3649) which specifically reactive to hamster immunoglobulins.

2. A hybridoma RHIg-87 (FERM BP-3649).

3. An immunoassay characterized in that the monoclonal antibody of claim 1 is labelled with a labelling substance, and used as a secondary antibody to a primary antibody or antiserum derived from hamster.

4. The immunoassay according to claim 3 in which the labelling substance is a fluorochrome, enzyme, or radioisotope.

5. An immunoassay characterized in that the monoclonal antibody of claim 1 is bound to biotin to form a first conjugate, the conjugate is reacted with a primary antibody or antiserum derived from hamster, and the product is then reacted with a second conjugate composed of a labelling substance and avidin or streptoavidin.

6. The immunoassay according to claim 5 in which the labelling substance is a fluorochrome, enzyme, or radioisotope.

* * * * *